(12) United States Patent
Zeller

(10) Patent No.: US 8,324,587 B2
(45) Date of Patent: *Dec. 4, 2012

(54) METHOD AND SYSTEM OF REDUCING FALSE TRIGGERING OF AN X-RAY SENSOR

(75) Inventor: Uwe Zeller, Biberach (DE)

(73) Assignee: Imaging Sciences International LLC, Hatfield, PA (US)

( * ) Notice: Subject to any disclaimer, the term of this patent is extended or adjusted under 35 U.S.C. 154(b) by 11 days.

This patent is subject to a terminal disclaimer.

(21) Appl. No.: 13/358,125

(22) Filed: Jan. 25, 2012

(65) Prior Publication Data

US 2012/0119099 A1      May 17, 2012

Related U.S. Application Data

(63) Continuation of application No. 12/605,624, filed on Oct. 26, 2009, now Pat. No. 8,119,990.

(60) Provisional application No. 61/108,552, filed on Oct. 27, 2008.

(51) Int. Cl.
*H01L 27/146* (2006.01)

(52) U.S. Cl. .................................. 250/370.09

(58) Field of Classification Search .............. 250/370.09
See application file for complete search history.

(56) References Cited

U.S. PATENT DOCUMENTS

| | | | |
|---|---|---|---|
| 4,057,732 A | 11/1977 | Klauser | |
| 4,259,583 A | 3/1981 | Albert | |
| 4,593,400 A | 6/1986 | Mouyen | |
| 4,866,750 A | 9/1989 | Chavarria et al. | |
| 5,331,166 A | 7/1994 | Crosetto et al. | |
| 5,434,418 A | 7/1995 | Schick | |
| 5,471,515 A | 11/1995 | Fossum et al. | |
| 5,510,623 A | 4/1996 | Sayag et al. | |
| 5,513,252 A | 4/1996 | Blaschka et al. | |
| 5,514,873 A | 5/1996 | Schulze-Ganzlin et al. | |
| 5,519,751 A | 5/1996 | Yamamoto et al. | |
| 5,574,250 A | 11/1996 | Hardie et al. | |
| 5,677,537 A | 10/1997 | Pfeiffer | |
| 5,691,539 A | 11/1997 | Pfeiffer | |
| 5,694,448 A | 12/1997 | Morcom | |
| 5,757,011 A | 5/1998 | Whitebook et al. | |

(Continued)

FOREIGN PATENT DOCUMENTS

DE        19815637        10/1998

(Continued)

OTHER PUBLICATIONS

International Search Report and Written Opinion, International Application No. PCT/US20101039322, mailed Aug. 17, 2010.

(Continued)

*Primary Examiner* — Christine Sung
(74) *Attorney, Agent, or Firm* — Michael Best & Friedrich LLP

(57) ABSTRACT

A system and method for automatic detection of x-rays at an x-ray sensor. A source emits x-ray radiation towards an x-ray sensor, and the x-ray sensor automatically detects the x-ray radiation. The x-ray sensor automatically detects x-ray radiation by evaluating a time series and determining that a voltage threshold is crossed a certain amount of time earlier than the average time it takes the voltage threshold to be crossed from dark current and other noise.

15 Claims, 11 Drawing Sheets

U.S. PATENT DOCUMENTS

| | | |
|---|---|---|
| 5,784,429 A | 7/1998 | Arai |
| 5,887,049 A | 3/1999 | Fossum |
| 5,894,129 A | 4/1999 | Pool |
| 5,912,942 A | 6/1999 | Schick et al. |
| 6,002,742 A | 12/1999 | Nelvig |
| 6,011,251 A | 1/2000 | Dierickx et al. |
| 6,030,119 A | 2/2000 | Tachibana et al. |
| 6,033,111 A | 3/2000 | Winters et al. |
| 6,042,267 A | 3/2000 | Muraki et al. |
| 6,069,935 A | 5/2000 | Schick et al. |
| 6,134,298 A | 10/2000 | Schick et al. |
| 6,169,781 B1 | 1/2001 | Doebert et al. |
| 6,203,195 B1 | 3/2001 | Willis |
| 6,244,866 B1 | 6/2001 | Campbell |
| 6,307,915 B1 | 10/2001 | Frojdh |
| 6,320,934 B1 | 11/2001 | Carroll et al. |
| 6,343,875 B1 | 2/2002 | Eppinger et al. |
| 6,404,854 B1 | 6/2002 | Carroll et al. |
| 6,462,268 B1 | 10/2002 | Hazy et al. |
| 6,527,442 B2 | 3/2003 | Carroll |
| 6,652,141 B1 | 11/2003 | Cianciosi |
| 6,744,068 B2 | 6/2004 | Fossum et al. |
| 6,797,960 B1 | 9/2004 | Spartiotis et al. |
| 6,811,312 B2 | 11/2004 | Bratslavsky et al. |
| 6,833,548 B2 | 12/2004 | Homme et al. |
| 6,898,268 B2 | 5/2005 | Makila et al. |
| 6,919,569 B2 | 7/2005 | Homme et al. |
| 6,924,486 B2 | 8/2005 | Schick et al. |
| 6,932,505 B2 | 8/2005 | Yao et al. |
| 6,972,411 B2 | 12/2005 | Schick et al. |
| 6,974,253 B2 | 12/2005 | Ihalainen |
| 7,006,600 B1 | 2/2006 | Krema et al. |
| 7,016,466 B2 | 3/2006 | Rinaldi et al. |
| 7,033,075 B2 | 4/2006 | Landis et al. |
| 7,036,985 B2 | 5/2006 | Puente et al. |
| 7,072,443 B2 | 7/2006 | Schick et al. |
| 7,090,395 B2 | 8/2006 | Glazer |
| 7,091,465 B2 | 8/2006 | Miyaguchi |
| 7,172,339 B2 | 2/2007 | Diederich |
| 7,193,219 B2 | 3/2007 | Schick et al. |
| 7,195,395 B2 | 3/2007 | Quarry et al. |
| 7,210,847 B2 | 5/2007 | Hack |
| 7,281,847 B2 | 10/2007 | Kokkaliaris et al. |
| 7,360,948 B2 | 4/2008 | Razzano et al. |
| 7,425,095 B2 | 9/2008 | Schmulenson et al. |
| 7,462,807 B2 | 12/2008 | Caupain et al. |
| 7,563,026 B2 | 7/2009 | Mandelkern et al. |
| 7,608,834 B2 | 10/2009 | Boucly et al. |
| 7,711,173 B2 | 5/2010 | Inglese |
| 7,915,589 B2 * | 3/2011 | Takenaka et al. ......... 250/361 R |
| 2004/0188625 A1 | 9/2004 | Schulze-Ganzlin |
| 2006/0257816 A1 | 11/2006 | Klemola et al. |
| 2006/0262461 A1 | 11/2006 | Wood |
| 2007/0147675 A1 | 6/2007 | Ulrici et al. |
| 2007/0176109 A1 | 8/2007 | Bell |
| 2007/0286335 A1 | 12/2007 | De Godzinsky |
| 2008/0001094 A1 | 1/2008 | Korthout et al. |
| 2008/0095321 A1 | 4/2008 | Calderwood et al. |
| 2008/0118028 A1 | 5/2008 | Stantchev |

FOREIGN PATENT DOCUMENTS

| | | |
|---|---|---|
| EP | 0415075 | 3/1991 |
| EP | 1230896 | 8/2002 |
| EP | 1252762 | 10/2002 |
| EP | 1255401 | 11/2002 |
| EP | 1378201 | 1/2004 |
| EP | 1623673 | 2/2006 |
| EP | 1746442 | 1/2007 |
| EP | 1803400 | 7/2007 |
| GB | 1514851 | 6/1978 |
| JP | 08-000603 | 1/1996 |
| WO | 92/22188 | 12/1992 |
| WO | 96/32064 | 10/1996 |
| WO | 01/58148 | 8/2001 |
| WO | 02/063338 | 8/2002 |
| WO | 03/032839 | 4/2003 |
| WO | 2006/004528 | 1/2006 |
| WO | 2006/008339 | 1/2006 |
| WO | 2006/034978 | 4/2006 |
| WO | 2006/089003 | 8/2006 |
| WO | 2006/093869 | 9/2006 |
| WO | 2006/103126 | 10/2006 |
| WO | 2007/003495 | 1/2007 |
| WO | 2007/022246 | 2/2007 |
| WO | 2007/030381 | 3/2007 |
| WO | 2007/044412 | 4/2007 |
| WO | 2007/142925 | 12/2007 |
| WO | 2008/058865 | 5/2008 |
| WO | 2008/103460 | 8/2008 |
| WO | 2009/055136 | 4/2009 |
| WO | 2009/058467 | 5/2009 |
| WO | 2009/058468 | 5/2009 |

OTHER PUBLICATIONS

International Search Report and Written Opinion, International Application No. PCT/US20101039324, mailed Oct. 8, 2010.

Andoh, F., et al., "A 250,000-Pixel Image Sensor with FET Amplification at Each Pixel for High-Speed Television Cameras", IEEE ISSCC Digest of Technical Papers, pp. 212-213, Feb. 1990.

Fossum, Eric R., "CMOS Image Sensors: Electronic Camera-On-A-Chip", IEEE Transactions on Electron Devices, vol. 44, No. 10, pp. 1689-1698, Oct. 1997.

Hong, Soonil, et al., "Development and Evaluation of a CMOS Sensor-Based Digital Intra-Oral Radiographic System", IEEE Transactions on Nuclear Science, vol. 52, No. 1, Feb. 2005.

Mendis, S.K., et al., "A 128×128 CMOS Active Pixel Image Sensor for Highly Integrated Imaging Systems", IEEE IEDM Technical Digest, pp. 583-586, 1993.

Nixon, R.H., et al., "128×128 CMOS Photodiode-Type Active Pixel Sensor with On-Chip Timing, Control and Signal Chain Electronics", SPIE, vol. 2415, pp. 117-123, 1995.

Spartiotis, Konstantinos, et al., "A Directly Converting High-Resolution Intra-Oral X-Ray Imaging Sensor", Nuclear Instruments and Methods in Physics Research, Section A, 501, pp. 594-601, Elsevier Science B.V., 2003.

Universal Serial Bus Specification, Chapter 6—Mechanical, Revision 2.0, Apr. 27, 2000.

* cited by examiner

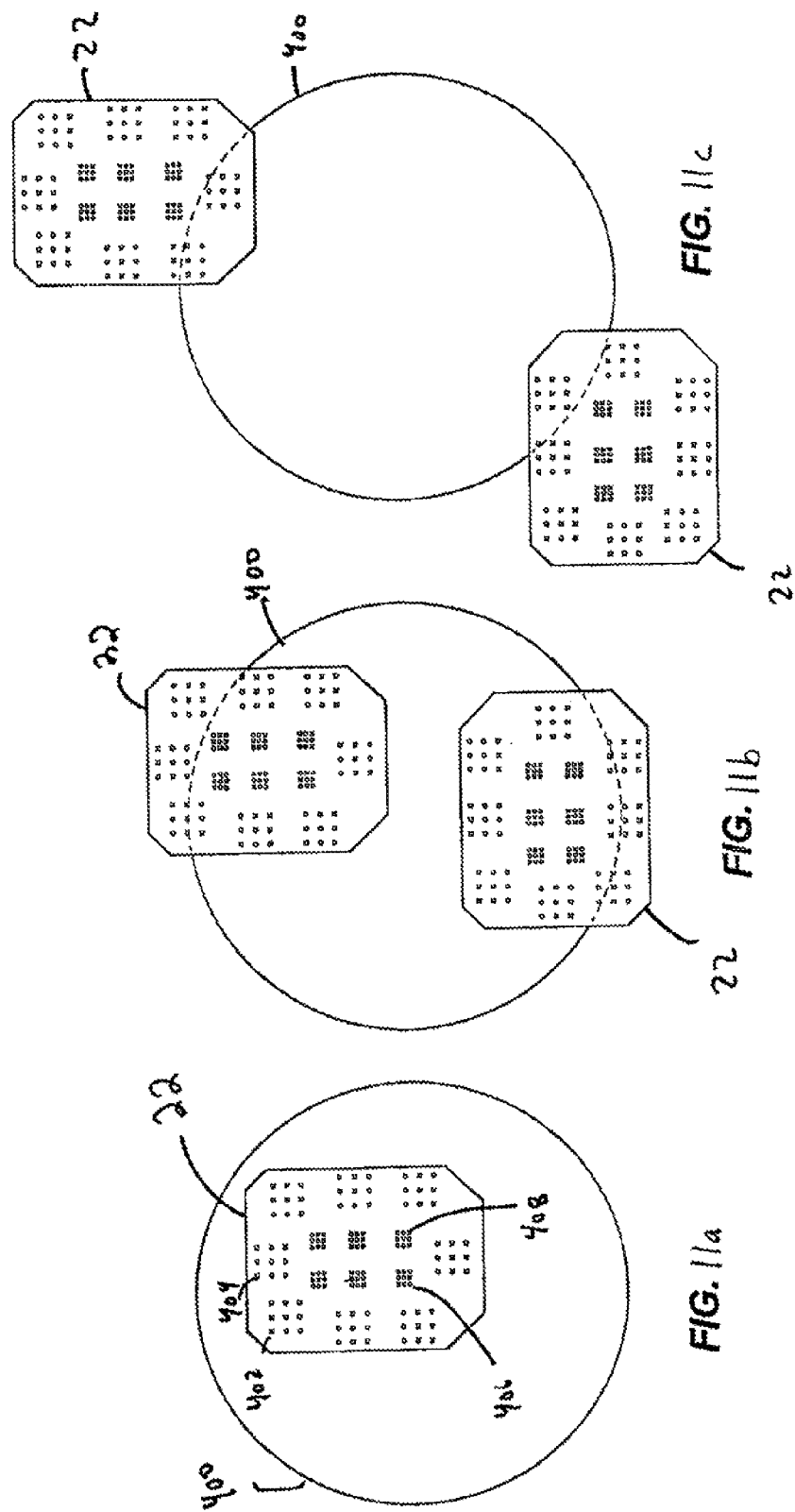

METHOD AND SYSTEM OF REDUCING FALSE TRIGGERING OF AN X-RAY SENSOR

RELATED APPLICATIONS

The present application is a continuation of Ser. No. 12/605,624, entitled SYSTEM AND METHOD OF X-RAY DETECTION WITH A SENSOR, filed on Oct. 26, 2009, the entire content of which is incorporated by reference herein.

BACKGROUND

The present invention relates to x-ray imaging. More particularly, embodiments of the invention relate to automatic triggering of an x-ray sensor used in dentistry.

X-rays have been used in dentistry to image teeth and parts of the mouth for many years. In general, the process involves generating x-rays outside the patient's oral cavity and directing the x-rays at an image receptor located in the patient's mouth. The x-rays are attenuated differently by different parts of the patient's dental structures (e.g., bone versus tissue) and this difference in attenuation is used to create an image, such as on film or by using an electronic image sensor. In most cases, the x-ray source is triggered manually by the operator. In other words, the capturing of an image is initiated by a technician or other person by, for example, activating a switch. In the case of film-based systems, the image is captured as soon as the film is exposed to x-ray radiation. So, there is no need to "activate" the film. Once the x-ray source is activated and the x-rays reach the film, an image is captured.

In electronic systems, the particular image captured depends on at least two factors: activation of the x-ray source and "activation" of the sensor. What constitutes "activation" of the sensor can vary based upon the type of sensor used, but in most cases "activation" occurs when a command is provided to the sensor to either store or output its current image data (referred to herein as "image capture"). So, in some systems, there is an electrical link between the x-ray source and the sensor such that when the x-ray source is activated, a command is sent (simultaneously or nearly simultaneously) to the sensor to perform an image capture. Thus, it is possible to generate a burst of x-ray radiation and be assured that an image will be captured by the sensor during the relatively short period of x-ray exposure.

SUMMARY

Embodiments of the invention provide automatic triggering of an x-ray sensor. In an automatic x-ray sensor, the sensor detects x-ray radiation from an x-ray source without requiring that a particular trigger signal be sent to the sensor. Although no particular triggering signal is sent to an automatic x-ray sensor, some initializing signals may be sent to the sensor to activate or arm the sensor and indicate it should begin waiting to detect x-ray radiation.

The inventors have recognized many challenges with respect to automatic triggering systems. One challenge relates to false triggering based on dark current accumulation. As an x-ray sensor waits to detect x-ray radiation from an x-ray source, dark current and other noise can build charge on the sensor and, eventually, cause the sensor to incorrectly determine x-ray radiation has been received. This false triggering issue is amplified as the ambient temperature near the sensor increases because dark current increases with temperature.

Another challenge associated with automatic triggering systems relates to the alignment between the x-ray source and the sensor. In many instances, even with the use of a positioning system or mechanism, x-ray sensors (particularly those placed in the mouth (i.e., an intra-oral sensor)) are often misaligned. Thus, only a portion of the x-ray sensor is exposed to radiation. In many instances, this partial exposure is not sufficient to cause a simple threshold-based trigger to initiate image capture. Thus, a misalignment may not be recognized until the x-ray technician attempts to review images that he or she believes to have been created only to discover that no such images have been created. The technician may then try to realign the x-ray source and sensor and reinitiate the imaging process. However, it may take several attempts to capture a usable image and each attempt exposes the patient to additional doses of x-ray radiation. As is well-known, high doses of x-ray radiation can have severe adverse effects on an individual's health. So, unnecessary exposure to x-rays should be avoided.

Yet another challenge associated with automatic triggering systems is the relatively large variation in x-ray doses and dose rates that are provided to perform x-ray image formation in a receptor. The variation in dosages and dose rates is caused by a number of factors including differences in x-ray sources. X-ray sources are manufactured by a number of different manufacturers and their designs and specifications have changed over time. Thus, the intensity of their outputs varies. For example, older x-ray machines usually generate relatively high x-ray doses with alternating dose rates while newer machines generate lower doses with more steady dose rates. The variation in x-ray doses and dose rates received at the sensor is also a consequence of variations in anatomy (from patient to patient) and the distance of the source to the patient. As is known, the dose is dependent on the distance (d) between the source and the patient by a factor of d2.

In one embodiment, the invention provides a method of automatically detecting x-ray radiation with an x-ray sensor. The method includes resetting a pixel array by removing stored charge from the pixel array and measuring, by a processor, an elapsed time since resetting of the pixel array. The method also includes a processor executing a decision operation using the elapsed time and an average dark current trigger time, and determining that a threshold has been crossed. The threshold being crossed indicates a predetermined amount of charge has been stored on at least a portion of the pixel array. The method also includes determining, by the processor, that x-ray radiation has been received at a portion of the pixel array based on the decision operation. Upon determining that x-ray radiation has been received, data is output from the pixel array to be used to generate an x-ray image.

In one embodiment, the invention provides an x-ray sensor that automatically detects receipt of x-rays. The x-ray sensor includes a processor, a pixel array, and a memory. The processor is configured to reset a pixel array by removing stored charge from the pixel array and measure an elapsed time since resetting of the pixel array. The processor is also configured to execute a decision operation using the elapsed time and an average dark current trigger time, and to determine that a threshold has been crossed. The threshold being crossed indicates a predetermined amount of charge has been stored on at least a portion of the pixel array. The processor is configured to determine that x-ray radiation has been received at a portion of the pixel array based on the decision operation. Upon determining that x-ray radiation has been received, the processor is configured to output data from the pixel array to be used to generate an x-ray image.

Other aspects of the invention will become apparent by consideration of the detailed description and accompanying drawings.

BRIEF DESCRIPTION OF THE DRAWINGS

FIGS. 11a-c illustrate a sensor receiving x-ray radiation.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Additionally, the term processor as is used in this application to mean any of a microcontroller, programmable logic device (e.g., a field programmable gate array "FPGA"), a general purpose processor, specifically designed hardware (e.g., an application specific integrated circuit "ASIC"), or a combination thereof.

Figure 1:
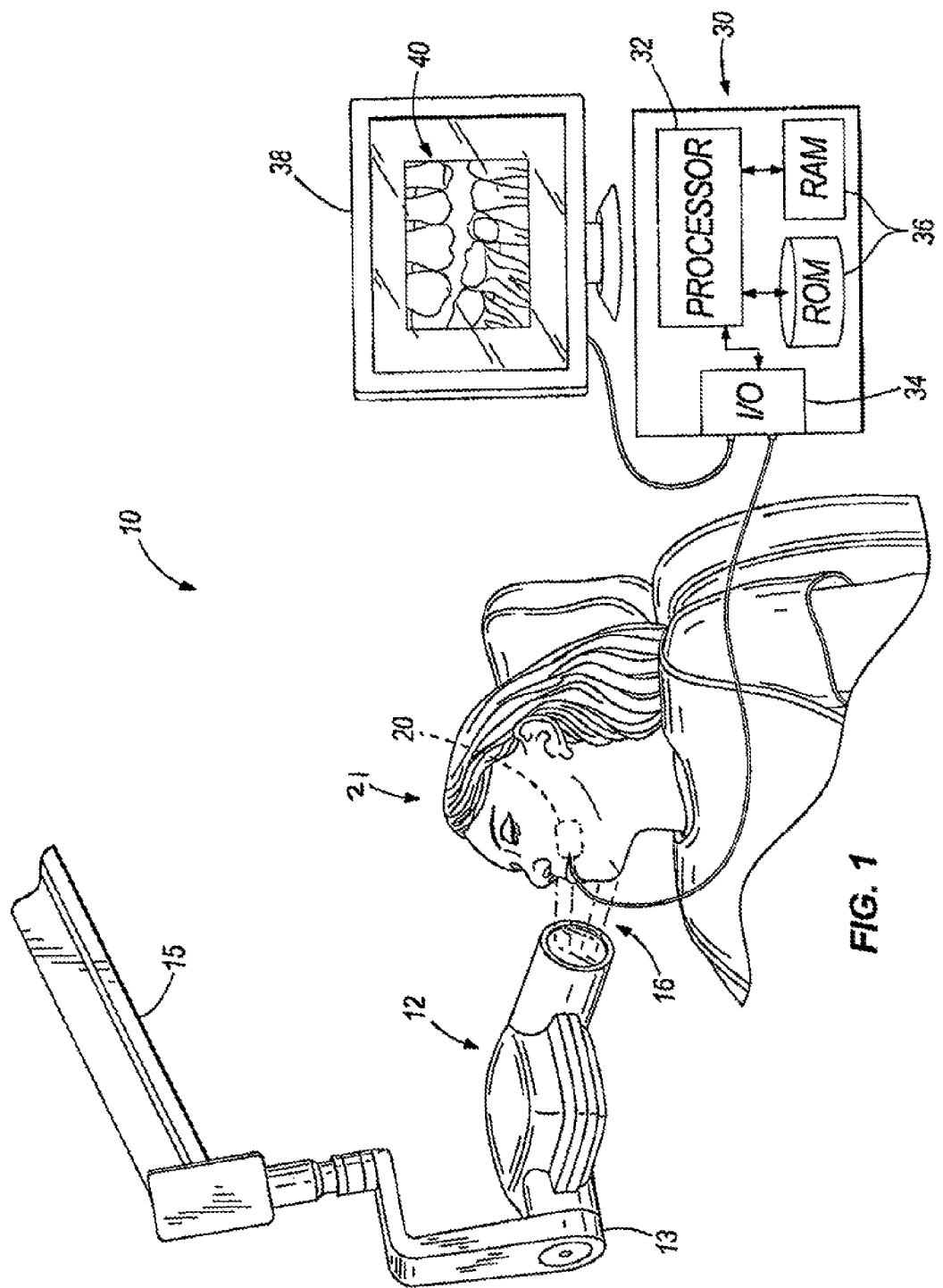
FIG. 1 illustrates a dental x-ray system including an x-ray source, an intraoral sensor located in a patient's mouth, and a computer connected to the intraoral sensor.

FIG. 1 illustrates a dental x-ray system 10. The system includes an x-ray source 12. In the embodiment shown, the source is located on an end 13 of a mechanical arm 15. When activated, the x-ray source 12 generates an x-ray stream 16. (Of course, x-rays are generally invisible, but a representation of a stream is illustrated to facilitate understanding of the invention.) In some applications, a removable collimator is used with a mechanical positioning device to help align the x-ray stream with an x-ray sensor.

As shown in FIG. 1, the arm 15 is positioned (e.g., by an operator) so that the x-ray stream is directed to an intraoral sensor 20. The intraoral sensor 20 is shown located in the mouth of a patient 21. In some embodiments, the intraoral sensor 20 includes a scintillator that coverts x-ray radiation to visible light and light detecting elements that convert the visible light to electrons. In other embodiments, the sensor 20 is configured to convert x-rays to electrons without a scintillator.

Figure 2:
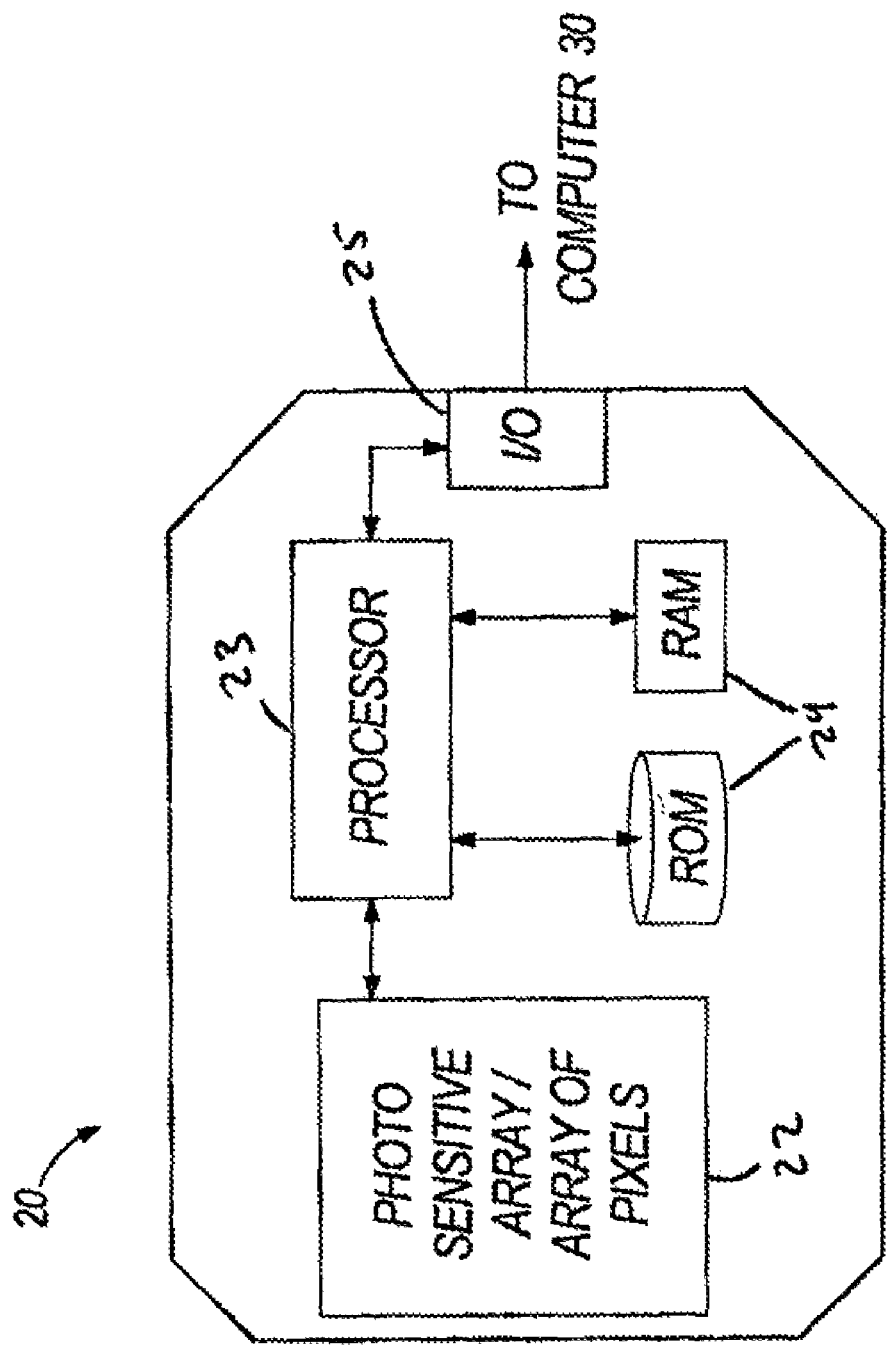
FIG. 2 illustrates an intraoral sensor.

As best seen by reference to FIG. 2, the sensor 20 also includes an array of pixels 22. Each pixel produces an electric signal in response to light (from the scintillator) or x-ray radiation impinged upon it. In one embodiment, the sensor 20 includes one or more analog-to-digital ("A/D") converters to covert analog signals generated by the pixels to digital signals. These signals are provided to a processor 23 (such as a programmable, electronic microprocessor, FPGA, ASIC, or similar device). In some embodiments, the A/D converters are implemented as part of the pixel array 22, as part of the processor 23, or as separate components between the pixel array 22 and the processor 23. In the embodiment shown, the processor 23 is connected to memory 24 (ROM and RAM) and an input-output interface 25. The sensor 20 also includes one or more electronic circuits for power supply, driving the pixel array, and driving the output (e.g., circuits located in the I/O interface 25). To facilitate the illustration of the connections between pixel array 22 and components 23, 24, and 25, the array 22 is shown as covering only a portion of the sensor 20. However, in most applications, the array 22 is generally coextensive with the sensor 20 and the components 23, 24, and 25 are located behind the array 22, rather than to the side of the array 22 (as shown in FIG. 2).

Referring back to FIG. 1, a wire, cable, or similar connector 27 of the sensor 20 connects the sensor 20 to a computer 30. The computer 30 includes various components, including a processor or similar electronic device 32, an input/output interface 34, and memory 36 (e.g., RAM and ROM). In one particular embodiment, the input/output interface 34 is a Universal Serial Bus ("USB") connection and the connector 27 is a USB cable. In other embodiments, a wireless connection is made between the sensor 20 and computer 30. FIG. 1 illustrates that image data captured by the sensor 20 and processed by the computer 30 is sent to a display 38 and viewed as image 40. (Image 40 is drawn more distinctly than an x-ray image would typically appear.)

Figure 3:
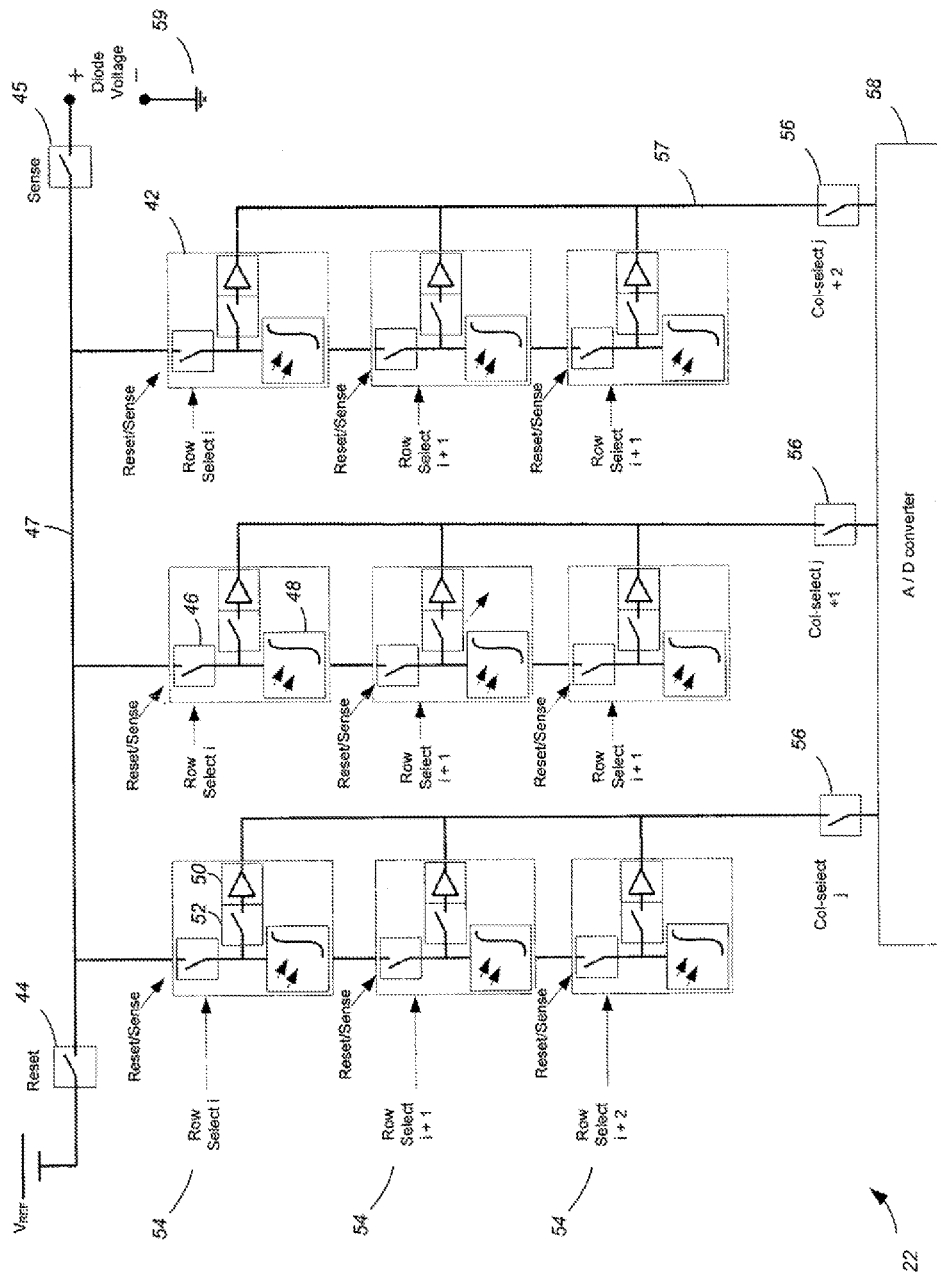
FIG. 3 illustrates a circuit diagram of a pixel array according to some embodiments of the invention.

FIG. 3 depicts an exemplary diagram of the pixel array 22. The pixel array 22 is depicted as a 3×3 pixel array for explanation purposes, but, the pixel array 22 generally has more than nine pixels. The pixel array 22 includes pixels 42, a reset switch 44, and a sensing switch 45. Each pixel includes a reset/sense switch 46, an integrating element 48, a read-out amplifier 50, and a read-out switch 52. The integrating element 48 integrates charge in response to receiving energy based on x-rays, dark current, and noise, as will be described in more detail below. While we use the term charge in this description, broadly speaking, the charge represents the amount of energy received at the integrating element 48. In other embodiments, electrons, holes, or other electrical signals, whether analog or digital, that represent the amount of energy received at the integrating element 48. Each pixel also receives one of the row select signals 54 and column select signals 56. The row select line 54 controls the read-out switch 52. The charge stored on each integrating element 48 can be read using the row select signals 54 and column select signals 56 and interpreted to generate an x-ray image 40 as described above. In some embodiments, the integrating element 48 is erased upon a read out (a "destructive" read). In other embodiments, the integrating element 48 is not erased upon a read out (a "non-destructive" read).

The pixel array 22 has four general function states: 1) a reset state, 2) a detecting state, 3) an integrating state, and 4) read-out state. In the reset state, the charge stored on the integrating element 48 of each pixel 42 is removed by setting the integrating elements 48 to the reference voltage (e.g., 2 volts). The integrating elements 48 are set to the reference voltage by closing the reset/sense switch 46 and the reset switch 44, while leaving the sense switch 45 and read-out switch 52 open.

In the detecting state, the reset/sense switch 46 and the sensing switch 45 are closed to connect integrating elements 48 to sensing line 47, while the reset switch 44 and the read-out switch 52 are left open. In the detecting state, the pixel array's collective charge is measured to determine whether a threshold has been crossed, which may indicate receipt of x-ray radiation. Each integrating element 48 begins with a voltage approximately equal to the reference voltage from the reset state. Thereafter, as charge is integrating at the integrating element 48 from x-ray energy, dark current, and noise, the voltage at the integrating element 48 decreases. Therefore, the collective voltage across the entire pixel array (referred to as the "diode voltage," since the entire pixel array 22 can be viewed as a meta diode) measured across the sense line 47 and ground 59 decreases as the voltage at any integrating element 48 decreases. In some embodiments, only a portion of the pixels 42 are connected to the sense switch 45 during the detecting state. In other embodiments, additional sense switches 45 are provided in the pixel array 22, and each sense switch 45 is connected to a particular portion of pixels 42. Thus, a particular portion of the pixels 42 may be sensed to have crossed a voltage threshold, as opposed to sensing across the entire pixel array 22.

In the integration state, all switches (44, 45, 46, and 52) are open. The pixel array 22 integrates the charges created by the x-ray radiation as well as by the undesirable noise components (e.g., dark current).

In the read-out state, a signal is provided to a column select line 56 (either j, j+1, or j+2). In addition, a signal is provided along a row select line 54 (either i, i+1, or i+2) to a particular row of pixels. In response, the read-out switches of the selected row of pixels is closed. The charge stored on the integrating elements 48 of the row of pixels is output along the output paths 57. The indication provided to the particular column select line 56 serves to chose one of the output paths 57 and allows the charge output along the chosen output path 57 to be input to the A/D converter 58. The A/D converter 58 converts the analog signal received from a pixel and outputs a digital signal to the processor 23. By repeating this process for each pixel 42 through providing signals to the appropriate row select line 54 and column select line 56, the entire pixel array 22 is read out.

In some embodiments, multiple pixels are read out in parallel. For instance, in some embodiments, the A/D converter 58 converts multiple analog signals from pixels 42 to digital signals simultaneously and forwards the digital signals along a multi-bit bus to the processor 23. In other embodiments, individual pixel A/D converters are provided within each pixel, as opposed to a single A/D converter 58. In some embodiments, the charge integrating on integrating elements 48 increases (rather than decreases) the voltage stored across each integrating element. In this embodiment, the reset signal removes the stored charge on each integrating element 48 by causing the voltage across each integrating element 48 to be set to ground. Additionally, the diode voltage increases, rather than decreases, as the pixel array is exposed to x-ray radiation, dark current, and other noise. Thus, the threshold voltage is set to a value above the reset value and is crossed upon the diode voltage increasing to a level above the threshold.

Figure 4:
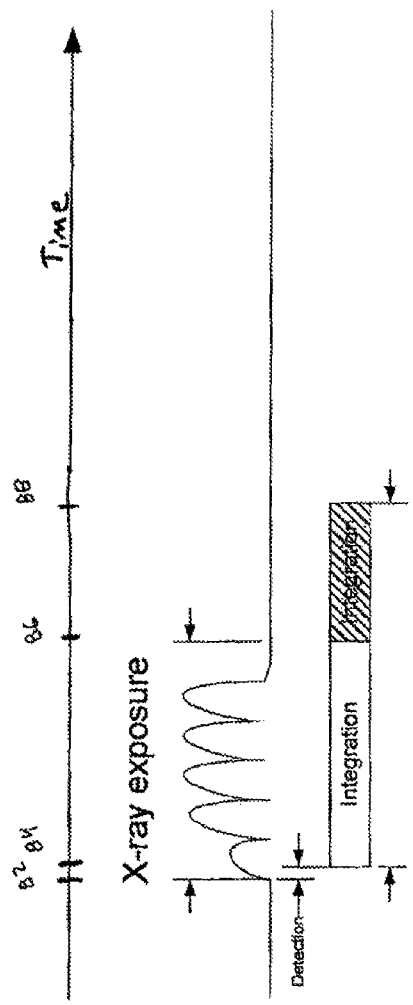
FIG. 4 depicts a timing diagram of x-ray exposure on a pixel array.

FIG. 4 depicts a time line 80 for the source 12 emitting an x-ray stream 16, the sensor 20 detecting the x-ray stream, and capturing of the image by the processor 23. Before time 82, the pixel array 22 is prepared by repeatedly switching between the reset state and detection state. At time 82, the source 12 begins to emit an x-ray stream 16. At time 84, the sensor 20 detects the x-ray stream 16 and begins integrating charge generated in response to the x-ray stream 16. At time 86, the x-ray radiation emitted from source 12 has concluded. Between times 86 and 88, the pixel array 22 remains in an integration state. In some embodiments, the integration time between times 86 and 88 is included to avoid a premature readout that would result in lost x-ray information. At time 88, the charge integrated at the pixel array 22 is read by the processor 23 and, in some embodiments, stored in memory 24. In one embodiment, the period between times 82 and 84 is in the range of 1 to 6 milliseconds; the period between times 84 and 86 is in the range of 20 to 600 milliseconds; the period between times 86 and 88 is in the range of about 200 hundred milliseconds; and the period between times 88 and the end of the pixel read out is approximately one second. Generally, the integration period between times 84 and 88 is set to be longer than the length of time the source 12 emits x-ray radiation. In some embodiments, however, the sensor 20 provides circuitry or software to detect the end of x-ray radiation and the read-out operation beginning at time 88 occurs before time 86 and closer to the end of the x-ray radiation.

The signal received at a pixel of pixel array 22 includes two main portions: a background signal and a signal generated as a result of incident x-ray radiation. The background signal is mostly a consequence of 1) dark current, 2) other parameters, and 3) noise. When the sum of the signals on the pixel array 22 cross a trigger threshold level, the sensor 20 detects an x-ray or performs additional steps to determine whether an x-ray has been received, as will be described below.

Figure 5:
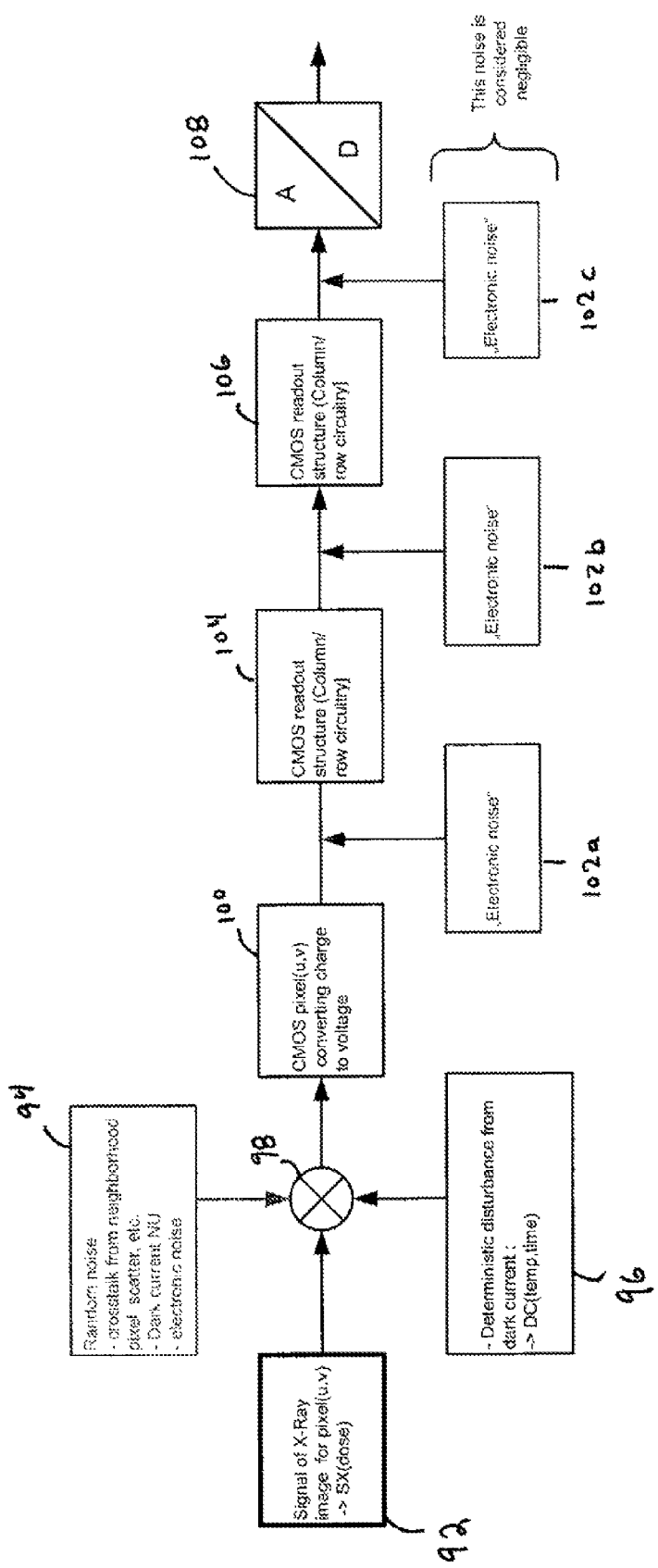
FIG. 5 depicts a flow chart of x-ray accumulation and output by a pixel.

FIG. 5 shows a model 90 of the x-ray accumulation and the signal output by a single pixel (u,v) of the pixel array 22. The charge built up on the pixel includes three components: 1) x-ray signals 92 from source 12, which may have been converted to light by a scintillator or similar device; 2) random noise 94 from various sources, and 3) dark current 96. The three components are integrated at the pixel, the function of which is represented at integrator 98. The integrator 98 is depicted as integrating element 48 in FIG. 3. The pixel, which is a CMOS device in one embodiment, converts the integrated charge into voltage at block 100. The block 100 is depicted as read-out amplifier 50 in FIG. 3. Thereafter, a read out of the pixel occurs in steps 104 and 106 by reading out the columns followed by the rows of the pixel array 22. Alternatively, the rows are read out followed a read out of the columns. Regardless of the column-row order, the voltage read out of the pixel array 22 is converted by an A/D converter 108, which may be within the pixel array or outside of the pixel array 22. The A/D converter 108 is depicted as A/D converter 58 in FIG. 3. Blocks 102a-c illustrate that the pixel array may also be subject to random noise, but the effect is normally negligible. Gain may be added to the signal either before the A/D 108, within the A/D 108, or digitally after the A/D 108.

Figure 6:
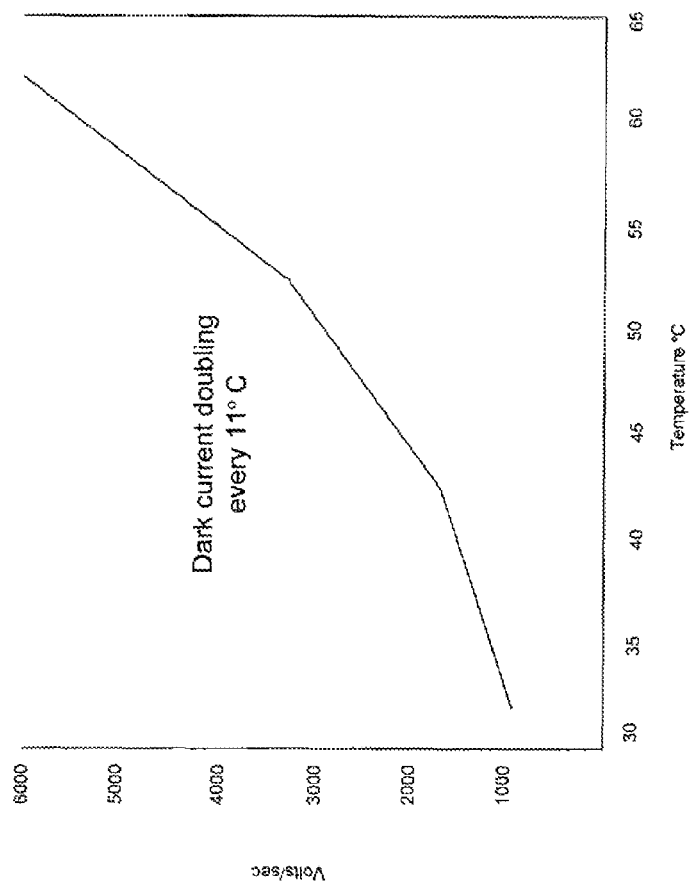
FIG. 6 depicts a graph of dark current relative to temperature.

FIG. 6 shows the influence of temperature on dark current as is known in the semiconductor imaging field. As the temperature of the pixel array 22 of sensor 20 increases (either on a particular portion or globally), the dark current increases. For instance, dark current doubles approximately every 7-11 degrees Celsius. The temperature of pixel array 22 can, for instance, increase when placed inside a patient's mouth for an intraoral x-ray, increase when exposed to sunlight, or decrease when exposed to a disinfectant (such as alcohol). The dark current, if allowed to accumulate, will eventually cause the trigger threshold of the pixel array 22 to be crossed and trigger an image capture when no x-rays have been received.

Figure 7:
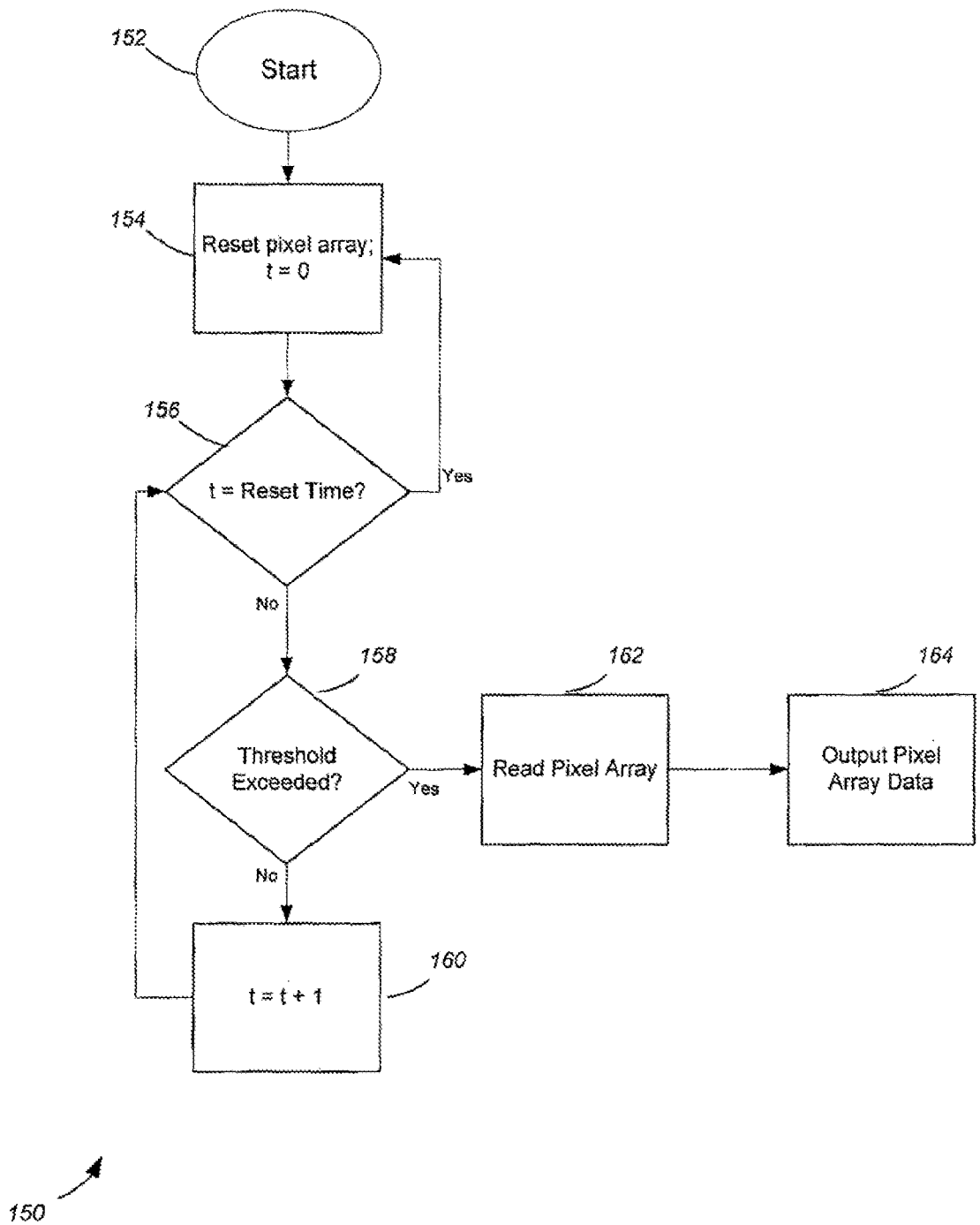
FIG. 7 illustrates a process of automatically detecting x-ray radiation.
Figure 8:
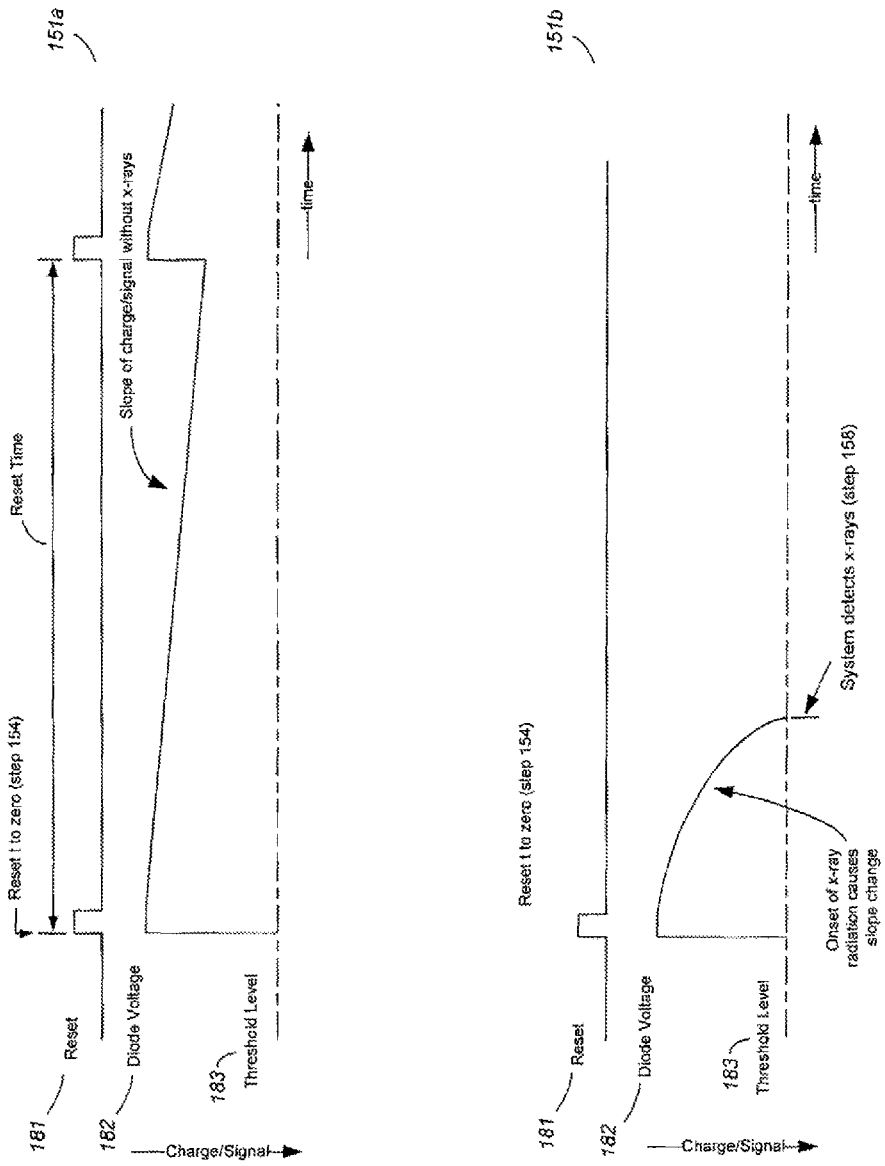
FIG. 8 illustrates fixed reset timing diagrams.

FIGS. 7 and 8 depict a process 150 of preventing dark current accumulation from falsely triggering pixel array 22 and fixed reset timing diagrams 151a and 151b. The process begins at step 152 and proceeds to a reset step 154. In the reset step 154, the variable "t" is reset to 0 and the pixel array 22 is reset. To reset the pixel array 22, the charge is drained off each pixel as described above with reference to FIG. 3. After the reset, charge begins to accumulate from sources such as dark current or an x-ray stream 16. In step 156, the process determines if variable t is equal to a predetermined "reset time." If the variable t is not equal to the reset time, the process proceeds to step 158. In step 158, the process determines whether charge accumulated in the pixel array 22 has exceeded the trigger threshold. If not, the process proceeds to step 160, where variable t is increased by one (i.e., t=t+1).

After step 160, the process returns to step 156 and again determines whether variable t is equal to the reset time. If no x-ray stream 16 is received by pixel array 22 over a predetermined amount of time (reset time), the process steps 156-160 will have repeated enough times such that t will equal reset time in step 156. Processing then proceeds to the reset step 154, and the pixel array 22 is reset such that dark current charge is eliminated from the pixel array 22. The process returns to steps 156-160 to await receipt of an x-ray stream 16. Exemplary reset times may be approximately 1 millisecond. The reset time may be stored in the processor 23 during manufacture of the sensor 20 or at another time before installation of the sensor 20 (installation occurs when the sensor is connected to a user's computer 30). In some embodiments, the reset time is updated in the field to accommodate for different x-ray doses and to account for aging and/or use of the sensor 20.

In step 158, if the charge accumulated in the pixel array 22 exceeds the trigger threshold, the process 150 determines that an x-ray stream 16 has been received by the pixel array 22. Thereafter, in step 162, the pixel array 22 is read by the processor 23 and, in step 164, output to the computer 30.

FIG. 8 depicts timing diagrams 151a and 151b for the reset signal 181 (sent to pixel array 22 during reset step 154) and the charge accumulation in pixel array 22. As charge accumulates in the pixel array 22, the diode voltage 182 declines from the initial value. As shown in timing diagram 151a, after the reset time passes (t=reset time in step 156), assuming no x-ray stream 16 has been received by the pixel array, the reset signal pulses and the pixel array 22 is reset. If, however, an x-ray stream 16 is received, the diode voltage will drop faster and cross below the threshold voltage 183 and the x-ray stream 16 will be detected (step 158), as shown in timing diagram 151b. In the embodiment shown in FIG. 8, a reset time of 300 microseconds, threshold voltage 183 of 0.5 V, and initial voltage of 2 V are used. In other embodiments, different values may be used.

Although the fixed-timing process 150 of FIG. 7 works in some instances, more adaptive techniques may be employed. If the chosen reset time is too long, dark current will accumulate and trigger an image capture when no x-ray stream has been received. If the chosen reset time is too short, not enough charge will be able to be integrated on the pixel array 22 to signify receipt of x-ray radiation. Thus, the trigger threshold will not be crossed and the x-ray stream 16 will not be detected. Furthermore, the reset time cannot automatically adjust for different environmental settings during operation. For instance, as shown in FIG. 6, dark current is highly dependent on temperature. The potential for temperature fluctuations increases the difficulty of selecting an appropriate reset time. Additionally, a reset time that is appropriate in a first setting may not be appropriate in a second setting. One additional issue is that different amounts of radiation may be emitted depending on the source 12, the distance between the source 12 and sensor 20, the alignment of the source 12 and sensor 20. As such, the reset time must be short enough to avoid false triggers by accumulated dark current and long enough to accommodate low doses of x-ray radiation.

Figure 9:
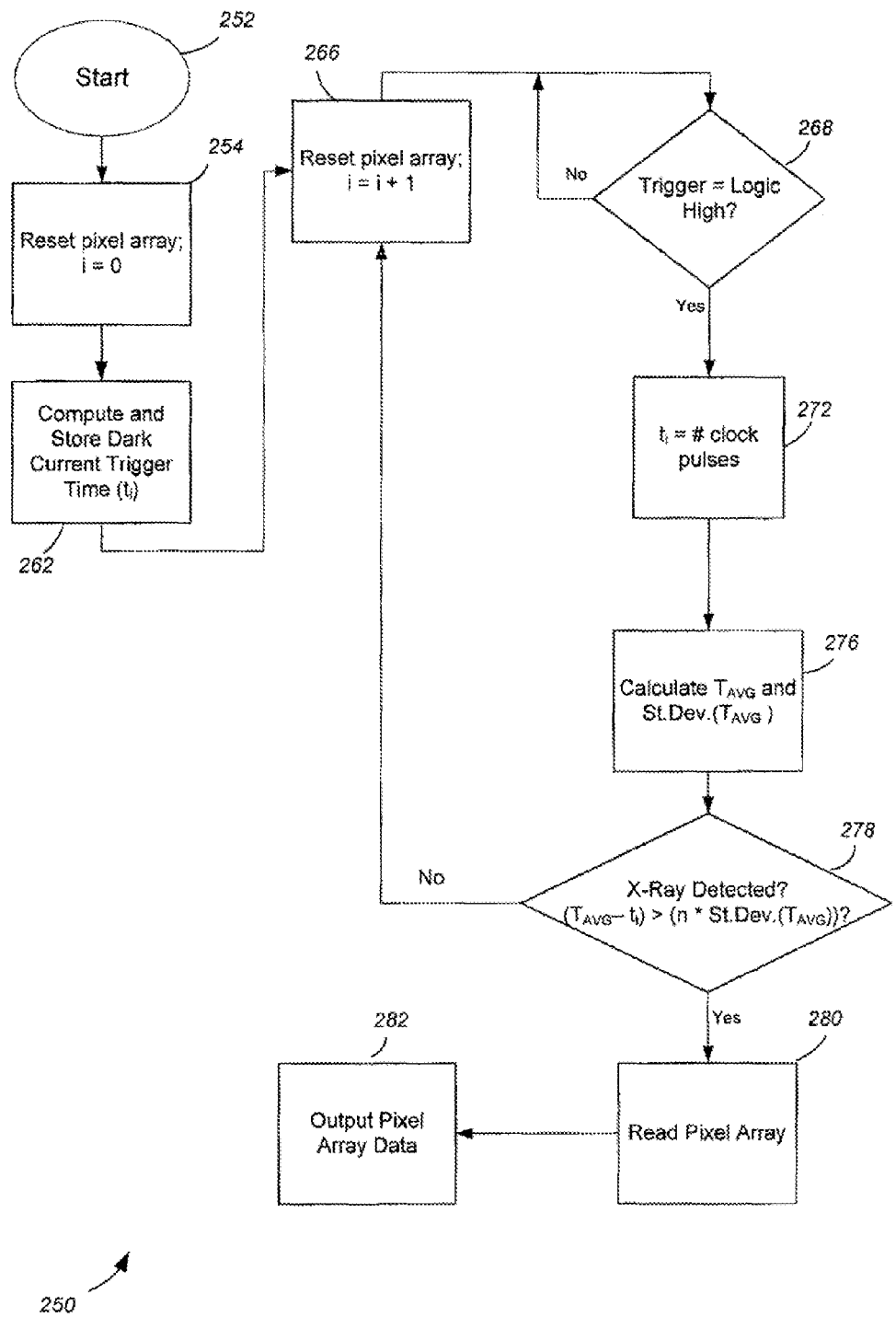
FIG. 9 illustrates a process of automatically detecting x-ray radiation.
Figure 10:
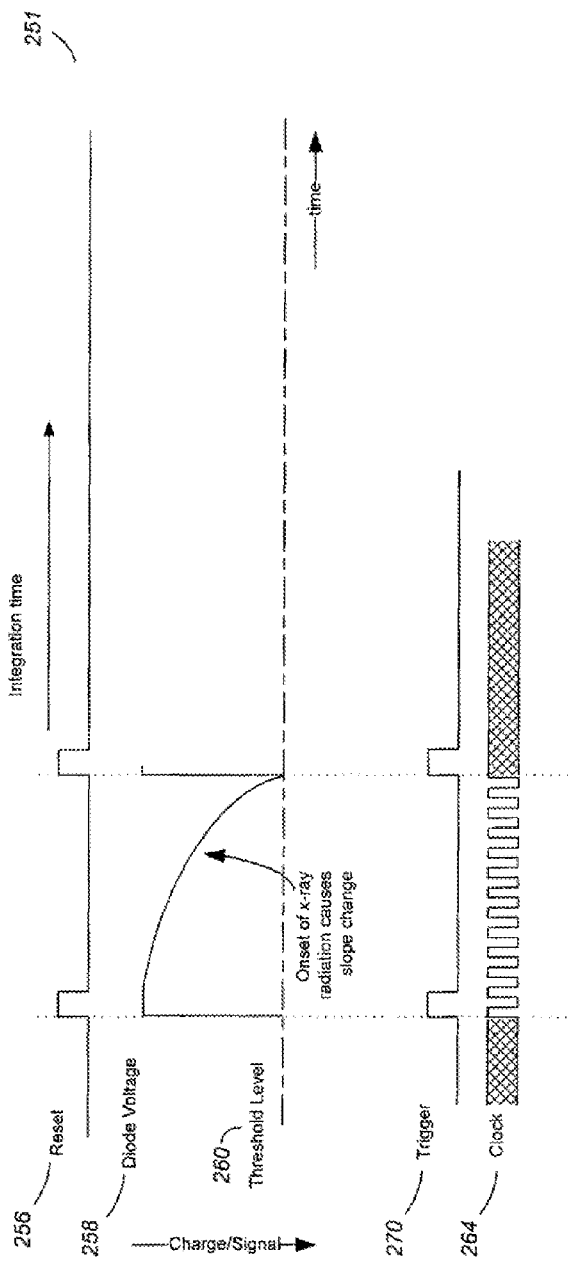
FIG. 10 illustrates a fully adaptive reset timing diagram.

FIGS. 9-10 depict an adaptive timing process 250 that address these concerns (FIG. 10 illustrates a timing diagram 251, which is discussed below). The process 250 of FIG. 9 begins at step 252 and proceeds to a reset step 254. In reset step 254, the variable i is reset to 0 and the pixel array 22 is reset by pulsing the reset signal 256. After the reset step, the sensor is allowed to accumulate dark current until the diode voltage 258 crosses the trigger threshold 260 in step 262. A counter counts the number of clock pulses 264 between the reset step 254 and the dark current causing the trigger threshold 260 to be crossed and sets $t_0$=number of clock pulses 264. This value $t_0$ is the initial dark current trigger time. The values of $t_i$ are also referred to as a "time series."

The process 250 proceeds to step 266, where the pixel array is again reset and i=i+1 by pulsing reset signal 256. In step 268, the process 250 determines whether the trigger threshold has been crossed by determining if the trigger value 270 has changed to a logic high. Step 268 is repeated until the trigger value 270 is changed to a logic high. Upon the trigger value 270 becoming a logic high, step 272 sets $t_i$=the number of clock pulses 264 that have elapsed since the reset step 266. In step 276, $T_{AVG}$ (the running average of $t_i$ from i=0 to i) is calculated. Additionally, the standard deviation of $T_{AVG}$ from time i=0 to i is calculated in step 276. $T_{AVG}$ represents the average dark current trigger time. The average dark current trigger time is the average elapsed time between a reset of the pixel array 22 and the diode voltage crossing the threshold 260 due to dark current. In some embodiments, $T_{AVG}$ is simply set equal to $t_{i-1}$ or is the running average of $t_i$ for only maximum number of previous $t_i$ values (e.g., $t_i$ from i=i−20 to i).

Thereafter, in step 278, $T_{AVG}-t_i$ is compared with a multiple of the standard deviation of $T_{AVG}$. If $T_{AVG}-t_i$ is greater than n times the standard deviation of $T_{AVG}$, an x-ray is detected. The value of fine tuning variable "n" is selected to adjust the detection process. In some embodiments, 0<n<1, meaning that small variations from the $T_{AVG}$ will result in an x-ray detection. In other embodiments, n>1, and only large variations from $T_{AVG}$ will result in an x-ray detection. In still other embodiments, n=1, and any variation from $T_{AVG}$ greater than the standard deviation will result in an x-ray detection. Upon detection of an x-ray, the process 250 proceeds to step 280, where the pixel array 22 is read by the processor 23 and, in step 282, output to the computer 30. If in step 278, however, $t_i-T_{AVG}$ is less than the product of n and the standard deviation of $T_{AVG}$, the process returns to step 266 to reset the pixel array and sets i=i+1.

In some embodiments, the comparison of step 278 simply compares the difference of $T_{AVG}$ and $t_i$ with a predetermined value (e.g., 0, 1, 2, etc.). If the difference between $T_{AVG}$ and $t_i$ is greater than the predetermined value, the method 250 will determine an x-ray has been received at the sensor 20.

In other embodiments, step 276 is replaced by a plurality of sub-steps (not shown), and each sub-step includes a comparison of the difference of $T_{AVG}$ and $t_i$ with a unique predetermined value (e.g., 0, 1, 2, etc.) or dynamic value (standard deviation). Using the plurality of comparisons enables the process 250 to detect both 1) high-dose rate, short duration x-ray exposures and 2) low-dose rate, long duration x-ray exposures. To detect high-dose rate, short duration exposures, one sub-step may include a detection algorithm that focuses only on the most recent $t_i$ values. To detect low-dose rate, long duration exposures, another sub-step may include a detection algorithm that analyzes $t_i$ values over a longer period of time. The sub-steps are executed in parallel and, if any sub-step indicates that an x-ray is detected, the process 250 proceeds to step 280. For instance, where variable X is greater than variable Y, a first sub-step for detecting a high-dose rate, short duration exposure, may detect an x-ray if the difference of $T_{AVG}$ and $t_i$ is greater than X. A second sub-step for detecting a low-dose rate, long duration exposure, may detect an x-ray if the differences of $T_{AVG}$ and $t_i$, $T_{AVG}$ and $t_{i-1}$, $T_{AVG}$ and $t_{i-2}$, $T_{AVG}$ and $t_{i-3}$, and $T_{AVG}$ and $t_{i-4}$ are all greater than Y. X and Y may be predetermined static values or may be based in part on dynamic values such as the standard deviations of $T_{AVG}$, but using different fine tuning variables n. A third sub-step may indicate an x-ray simply by determining that the difference between $t_i$ and $t_{i-1}$ is greater than a variable Z. In this third sub-step, the variable Z should be relatively large such that it is greater than any likely variation caused merely by noise.

In some embodiments, steps 262 and 268 have timeout limits whereby the sensor 20 will produce a timeout signal after a predetermined amount of time if the threshold 260 is not crossed. Thus, the timeout limits prevent the sensor 20 from waiting an infinite amount of time when an error prevents the threshold 260 from being crossed.

In some embodiments, the $T_{AVG}$ or $t_i$ value are used by the processor 23 as an indication that the sensor 20 is over-heated (i.e., from being exposed to direct sunlight). For instance, if $T_{AVG}$ is too low, either in a single instance or over a predetermined number of iterations of dark current causing the diode voltage to cross the threshold 260, the processor 23 concludes that the sensor 20 is over-heated. Appropriate warning signals, alerts, or other information is provided to a user upon detecting that the sensor 20 is over-heated.

Referring now to FIG. 10, the timing diagram 251 includes trigger value 270, which indicates that the diode voltage 258 has crossed the trigger threshold 260. A time is measured by, for instance, counting clock pulses 264. The variable $t_i$ is then set to the number of clock pulses counted, as described for process 250. The reset signal 256 pulses to reset the pixel array 22 and to reset the diode voltage 258. In the embodiment shown in FIG. 10, a trigger threshold 260 of 0.5 V and initial diode voltage 258 of 2 V are used. In other embodiments, different values are used.

In some embodiments of process 250, the sensor 20 is configured to be in an armed state or disarmed state. When the sensor 20 is in a disarmed state, the process 250 proceeds normally except that the decision in step 278 is always determined to be false and the process returns to step 266 regardless of the values of $T_{AVG}$, $t_i$, n, and the standard deviation of $T_{AVG}$. When sensor 20 is armed, the decision in step 278 is executed normally (if $T_{AVG}-t_i$ is greater than the product of the tuning variable n and the standard deviation of $T_{AVG}$ the process proceeds to step 280). However, the values calculated while the sensor 20 was disarmed continue to be used in the armed state In some embodiments, a constant gain level is applied to the data output from the pixel array 22. The gain level alters the rate of change 259 of the diode voltage 258 (see FIG. 10). For instance, a higher gain level will increase the rate of change 259 such that less charge integration at the integrating elements 48 is necessary to cause crossing of the threshold voltage 260. A lower gain level, in contrast, will decrease the rate of change 259 such that more charge integration at the integrating elements 48 is necessary to cause crossing of the threshold voltage 260. In some embodiments, the gain level is altered based on $t_i$ levels. For instance, if $t_i$ levels are too short, the gain level may be decreased causing the average dark current time to increase. Generally, the result will include a greater difference between $T_{AVG}$ (average dark current time) and the $t_i$ value when an x-ray is received at the sensor. If $t_i$ levels are too long, the gain level may be increased such that enough x-ray associated charge is integrated to generate a low noise x-ray image.

In some embodiments, the average dark current trigger times calculated in processes 250 are used by the processor 23 to estimate the temperature at which the sensor 20 is operating. The calculated temperature can be used, among other reasons, to create temperature records of the sensor 20 and to warn the user that the sensor 20 is operating at a temperature outside of acceptable temperature ranges. The temperature records are used to identify thermal stresses placed on the sensor 20 (e.g., stresses caused by spraying the sensor with a disinfectant) or for other maintenance analysis. Furthermore, the calculated temperature can be used to scale an offset image of the sensor 20, predict an offset image of the sensor 20, or both.

In other embodiments, a desired integration time for the pixel array 22 is estimated by analyzing the time $t_i$ between a reset of the pixel array 22 to the receipt of x-rays at the pixel array 22 (as determined by method 250). The time $t_i$ is analyzed to estimate the dose rate. The shorter the higher the estimated dose rate because of the reduced amount of time it took for the threshold to be crossed. Once an estimated dose rate is determined, the integration time (i.e., the time between times 84 and 88 of FIG. 4) can be properly adjusted. For example, if the processor 23 estimates a high dose rate, a shorter integration time is used. If the processor 23 estimates a low dose rate, a longer integration time is used. Adjusting the integration time based on an accurately estimated dose rate results in less dark current in the pixel array 22 from long integration times, yet prevents short integration times that cut-off integration of x-ray signals too early.

The processes 150 and 250 use detection processes based on the cumulative charge across the entire pixel array 22. While measuring the charge on the entire pixel array provides adequate detection in some situations, the level of the cumulative charge integration is altered if the x-ray field does not cover the entire pixel array 22. When the x-ray field does not cover the entire pixel array 22 (also referred to as a "cone cut"), the amount of integration due to x-rays is reduced proportionally to the portion of the pixel array 22 that was not covered, but the effects of dark current are still integrated across the entire pixel array 22. Thus, x-rays may not be detected if the x-ray source is not properly aligned to the pixel array 22. For instance, in FIG. 11a, the x-ray source 12 is properly aligned and the pixel array 22 is completely within a circle 400 of x-ray stream 16. In FIGS. 11b and 11c, however, the circle 400 of x-ray stream 16 does not reach the entire pixel array 22. Rather, only a portion of the pixel array 22 receives x-ray radiation. If less than the entire pixel array 22 receives x-ray radiation, a lower amount of charge will be built up on the pixel array 22 than if the entire pixel array was within the circle 400 (as shown, for example, in FIG. 11a). Thus, in FIGS. 11b and 11c, the trigger threshold may not be crossed despite receipt of x-ray radiation.

In some embodiments, to account for misaligned x-ray sources, the detection processes 150 and 250 monitor multiple sections of the pixel array 22 independently. For instance, the pixel array 22 of FIGS. 11a-c includes 14 sections, four of which are labeled sections 402, 404, 406, and 408 for exemplary purposes. Thus, if an x-ray is detected on any of the sections, the processes will detect an x-ray for the entire pixel array 22 and an image capture will take place. Thus, the automatic detection processes account for a misaligned x-ray source 12 and sensor 20.

In some embodiments, one or more of the plurality of sections of the pixel array 22 being independently monitored are kept in the detecting mode after detection of x-rays, while the remainder of the pixel array 22 sections are switched to the integration mode. The information provided by the few sections that remain in the detecting mode can be used to 1) confirm no false trigger has occurred, 2) detect A/C x-ray pulse patterns, and 3) detect the end of x-ray radiation being received at the pixel array 22. As discussed above, detecting the end of x-ray radiation can be used to more closely tailor the duration of integration of the pixel array 22 to the duration of x-ray exposure. More closely tailoring the duration of integration reduces the time period between times 84 and 88 to more closely match the duration of the x-ray exposure.

Although the detection processes described above are directed to human dentistry, in some embodiments the processes are used with x-ray sensors intended for: veterinary applications; non-dental applications; and imaging of inanimate objects. Furthermore, in some embodiments, the processor 23 and memory 24 of sensor 20, or their associated functions, reside or are executed within the computer 30.

Although the timing diagrams and processes were described with particular logic states, e.g., logic high and logic low, embodiments of the invention contemplate using alternative signal orientations to signal similar events. For instance, the trigger value 270 becomes a logic high upon the diode voltage 258 crossing trigger threshold 260 in FIG. 10. However, in some embodiments, the trigger value 270 becomes a logic low to indicate the trigger threshold 260 has been crossed.

Thus, the invention provides, among other things, systems and methods for automatic detection of x-rays. Various features and advantages of the invention are set forth in the following claims.

What is claimed is:

1. A method of automatically detecting x-ray radiation with an x-ray sensor, the method comprising:
   resetting a pixel array;
   determining a dark current time;
   measuring an elapsed time since resetting of the pixel array;
   performing a comparison; and
   determining that x-ray radiation has been received at at least a portion of the pixel array based on the comparison.

2. The method of claim 1, wherein performing the comparison includes comparing a difference between the elapsed time and the dark current time with at least one of
   a predetermined value, and
   a product of a fine tuning variable and a standard deviation of the dark current time.

3. The method of claim 2, wherein x-ray radiation is determined to have been received at the at least a portion of the pixel array if the difference is greater than the at least one of the predetermined value or the standard deviation.

4. The method of claim 1, wherein the dark current time is determined based on iteratively calculating an elapsed time between a reset of the pixel array and a determination that a trigger threshold has been crossed.

5. The method of claim 1, wherein the dark current time indicates a temperature of the x-ray sensor.

6. The method of claim 5, further comprising generating an error condition if the temperature of the x-ray sensor indicated by the dark current exceeds a predetermined level.

7. The method of claim 1, further comprising determining that a trigger threshold has been crossed, wherein the threshold is a predetermined voltage level, and wherein the predetermined amount of charge stored on the at least a portion of the pixel array causes a voltage potential at a diode to drop below the threshold.

8. The method of claim 1, further comprising
   determining that x-ray radiation is no longer being received, and
   reducing an integration time for a subsequent x-ray radiation exposure based on a duration of x-ray radiation received at the at least a portion of the pixel array.

9. An x-ray sensor that automatically detects receipt of x-rays, the x-ray sensor including a processor and a pixel array, the processor configured to:
   reset the pixel array;
   determine that a trigger threshold has been crossed,
   measure an elapsed time since resetting of the pixel array;
   determine an average dark current trigger time;
   perform a comparison based upon the elapsed time and the average dark current trigger time;
   determine that x-ray radiation has been received at at least a portion of the pixel array based on the comparison; and
   upon determining that x-ray radiation has been received, output data from the pixel array to be used to generate an x-ray image.

10. The x-ray sensor of claim 9, wherein the processor is further configured to perform the comparison by comparing a difference between the elapsed time and the average dark current trigger time with at least one of
    a predetermined value, and
    a product of a fine tuning variable and a standard deviation of the average dark current trigger time.

11. The x-ray sensor of claim 10, wherein x-ray radiation is determined to have been received at the at least a portion of the pixel array if the difference is greater than the at least one of the predetermined value or the standard deviation.

12. The x-ray sensor of claim 11, wherein the average dark current trigger time is based on iteratively calculating an elapsed time between a reset of the pixel array and a determination that the threshold has been crossed due to dark current.

13. The x-ray sensor of claim 9, wherein the average dark current trigger time indicates a temperature of the x-ray sensor.

14. The x-ray sensor of claim 13, wherein the processor is further configured to generate an error condition if the temperature of the x-ray sensor indicated by the average dark current trigger time exceeds a predetermined level.

15. An x-ray sensor that automatically detects receipt of x-rays, the x-ray sensor including a processor and a pixel array, the processor configured to:
    reset the pixel array;
    determine that a trigger threshold based on dark current has been crossed,
    measure an elapsed time since resetting of the pixel array;
    determine an average dark current trigger time;
    perform a comparison based upon the elapsed time and the average dark current trigger time;
    determine that x-ray radiation has been received at at least a portion of the pixel array based on the comparison; and
    upon determining that x-ray radiation has been received, output image data from the pixel array.

* * * * *